United States Patent
Conston et al.

(10) Patent No.: US 8,491,549 B2
(45) Date of Patent: Jul. 23, 2013

(54) OPHTHALMIC MICROSURGICAL SYSTEM

(75) Inventors: Stanley R. Conston, San Carlos, CA (US); Ronald K. Yamamoto, San Francisco, CA (US)

(73) Assignee: IScience Interventional Corporation, Menlo Park, CA (US)

( * ) Notice: Subject to any disclaimer, the term of this patent is extended or adjusted under 35 U.S.C. 154(b) by 2872 days.

(21) Appl. No.: 10/496,254

(22) PCT Filed: Nov. 21, 2002

(86) PCT No.: PCT/US02/37572
§ 371 (c)(1),
(2), (4) Date: May 20, 2004

(87) PCT Pub. No.: WO03/045290
PCT Pub. Date: Jun. 5, 2003

(65) Prior Publication Data
US 2006/0149194 A1 Jul. 6, 2006

Related U.S. Application Data

(60) Provisional application No. 60/331,970, filed on Nov. 21, 2001.

(51) Int. Cl.
*A61M 35/00* (2006.01)
*A61M 5/00* (2006.01)

(52) U.S. Cl.
USPC ............................. 604/294; 604/264

(58) Field of Classification Search
USPC ................................... 604/294, 264
See application file for complete search history.

(56) References Cited

U.S. PATENT DOCUMENTS 6,402,734 B1 * 6/2002 Weiss ........................... 604/521
2001/0053873 A1 * 12/2001 Schaaf et al. ................. 600/104

* cited by examiner

*Primary Examiner* — Victoria P Shumate
(74) *Attorney, Agent, or Firm* — GSS Law Group; James J. Leary; Carol D. Titus

(57) ABSTRACT

An ophthalmic microsurgical system is described for treatment of eye diseases, such as glaucoma, using minimally invasive surgical techniques. The microsurgical system includes a thin walled outer sheath microcannula 1 slidably disposed about an inner member 4, which extends slightly beyond the distal end of the microcannula 1. The inner member 4 may be straight or curved and may optionally include a surgical instrument and/or a sensor or signaling beacon. The microsurgical system is used in a surgical procedure for opening Schlemm's Canal to provide drainage of aqueous fluid in order to relieve excess intraocular pressure that results from glaucoma and other diseases of the eye.

24 Claims, 3 Drawing Sheets

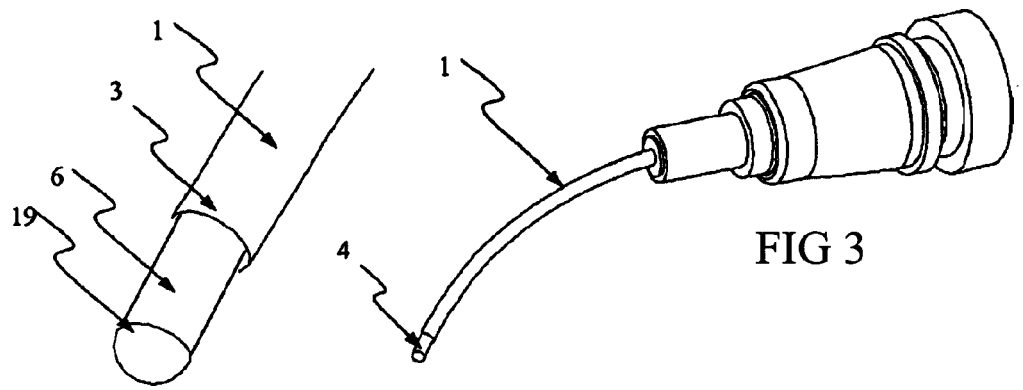
FIG 3
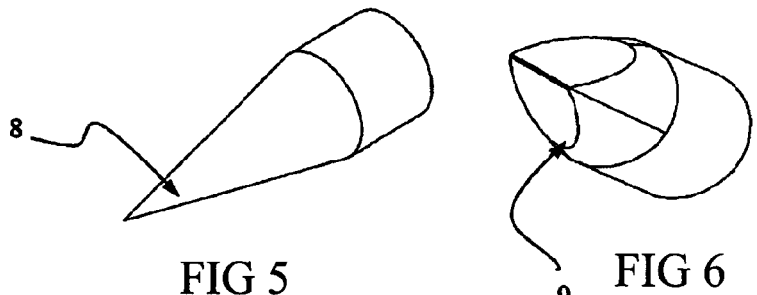
FIG 4
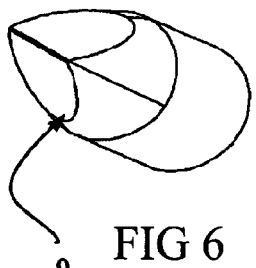
FIG 5
FIG 6
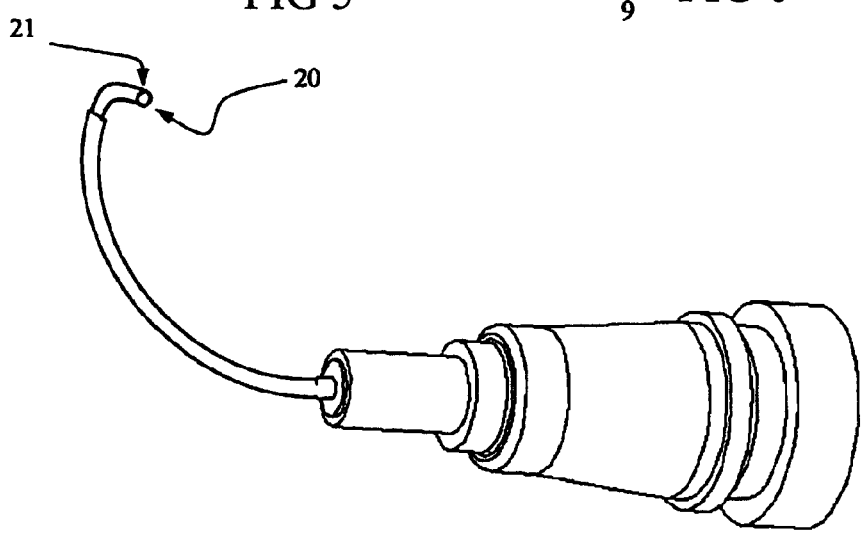
FIG 7

OPHTHALMIC MICROSURGICAL SYSTEM

CROSS REFERENCE TO RELATED APPLICATIONS

The present application is a National Stage Entry of PCT/US02/37572, which claims priority to U.S. Provisional Application 60/331,970 filed Nov. 21, 2001, both of which are incorporated by reference herein.

FIELD OF THE INVENTION

The present invention relates to a microsurgical system for treatment of eye diseases, such as glaucoma, using minimally invasive surgical techniques.

BACKGROUND OF THE INVENTION

Glaucoma is a disease condition of the eye in which increased intraocular pressure (IOP) is created by reduction or blockage of the drainage mechanism for the aqueous fluid produced in the anterior portion of the eye. Such conditions are usually treated by topical drugs in the form of eye drops, but may result in surgical treatment if drug treatment becomes ineffective or if patient compliance is an issue. Traditional glaucoma surgery, such as a trabeculotomy or trabeculectomy, involve dissection of the eye and the forming of new passages through or near the trabecular meshwork portion of the drainage pathway and directing the fluid to a subconjunctival pocket known as a bleb. Although effective for a short period, long-term follow-up of these treatments shows marked increases in intraocular pressure and therefore low success rates. Other serious complications include hypotony, in which too much drainage is accomplished and the IOP drops to sight threatening levels. These procedures also involve post surgical complications, such as infection and long-term issues related to bleb management.

A recently developed surgical treatment for glaucoma is known as viscocanalostomy. The procedure involves surgically opening a flap of the sclera and dissecting down to de-roof Schlemm's canal to increase aqueous humor drainage. A high viscosity viscoelastic material is injected into the canal to dilate it, and may act to open the trabecular meshwork from the canalicular space. The viscoelastic material may also act as a fibrosis inhibitor, reducing the influx of fibroblastic cells from the healing response, which would negate the effects of the procedure by blocking fluid flow. Stegmann, et al. in U.S. Pat. No. 5,486,165 discloses a microcannula designed for delivery of substances to Schlemm's canal during this procedure. In EP 089847, Grieshaber, et al. disclose an improvement to the Stegmann apparatus to deliver substances or stents for maintaining the passage of fluid in the canal.

Other surgical procedures, such as non-penetrating deep sclerectomy and trabeculectomy involve accessing and treating the aqueous drainage system in various manners. Minimally invasive access to the requisite tissues involved in aqueous fluid drainage, such as the trabecular meshwork, Schlemm's Canal, aqueous collector channels and aqueous veins can provide treatment with fewer complications.

The invention is directed at an ophthalmic microsurgical system comprised of a microcannula and associated microsurgical tools, which may be directly inserted into the sclera, Schlemm's Canal, aqueous collector channels, aqueous veins or other ocular tissues to allow minimally invasive access and progressive treatment with surgical materials and tools.

The following patent documents relate to methods and apparatus for treatment of glaucoma and other ocular diseases.

U.S. Pat. No. 5,360,399 METHOD AND APPARATUS FOR MAINTAINING THE NORMAL INTRAOCULAR PRESSURE, inventor Robert Stegmann U.S. Pat. No. 5,486,165 METHOD AND APPLIANCE FOR MAINTAINING THE NATURAL INTRAOCULAR PRESSURE, inventor Robert Stegmann U.S. Pat. No. 6,142,990 MEDICAL APPARATUS, ESPECIALLY FOR REDUCING INTRAOCULAR PRESSURE, inventor Reinhard O. W. Burk WO 0064389 TRABECULOTOMY DEVICE AND METHOD FOR TREATING GLAUCOMA, inventors Brown Reay H, Lynch Mary G, King Spencer B III WO 02/089699 MEDICAL DEVICE AND METHODS FOR USE FOR GLAUCOMA TREATMENT, inventors Tu Hosheng, Smedley Gregory, Niksch Barbara, Haffner David WO 02/080811 GLAUCOMA STENT AND METHODS THEREOF FOR GLAUCOMA TREATMENT, inventors Tu Hosheng, Smedley Gregory, Niksch Barbara, Haffner David WO 02/070045 GLAUCOMA TREATMENT DEVICE AND METHOD, inventors Brown David, Anderson Richard U.S. Pat. No. 6,471,666 INJECTABLE GLAUCOMA DEVICE, inventor Odrich Steven U.S. Pat. No. 6,464,724 STENT DEVICE AND METHOD FOR TREATING GLAUCOMA, inventors Lynch Mary, Brown Reay WO 01/78656 DEVICE FOR GLAUCOMA TREATMENT AND METHODS THEREOF, inventor Hill Richard

BRIEF DESCRIPTION OF THE DRAWINGS

FIG. 3 shows an assembled view of the outer sheath microcannula and the inner member of the ophthalmic microsurgical system.

FIG. 4 is an enlarged detail drawing of the distal tip of the outer sheath microcannula and the inner member shown in FIG. 3.

FIG. 5 is an enlarged detail drawing of an inner member with a conical distal cutting tip.

FIG. 6 is an enlarged detail drawing of an inner member with a spatula shaped distal cutting tip.

FIG. 7 shows an inner member that includes a surgical tool for creating controlled punctures in the trabecular meshwork from within Schlemm's Canal.

DESCRIPTION OF THE INVENTION

Figure 1:
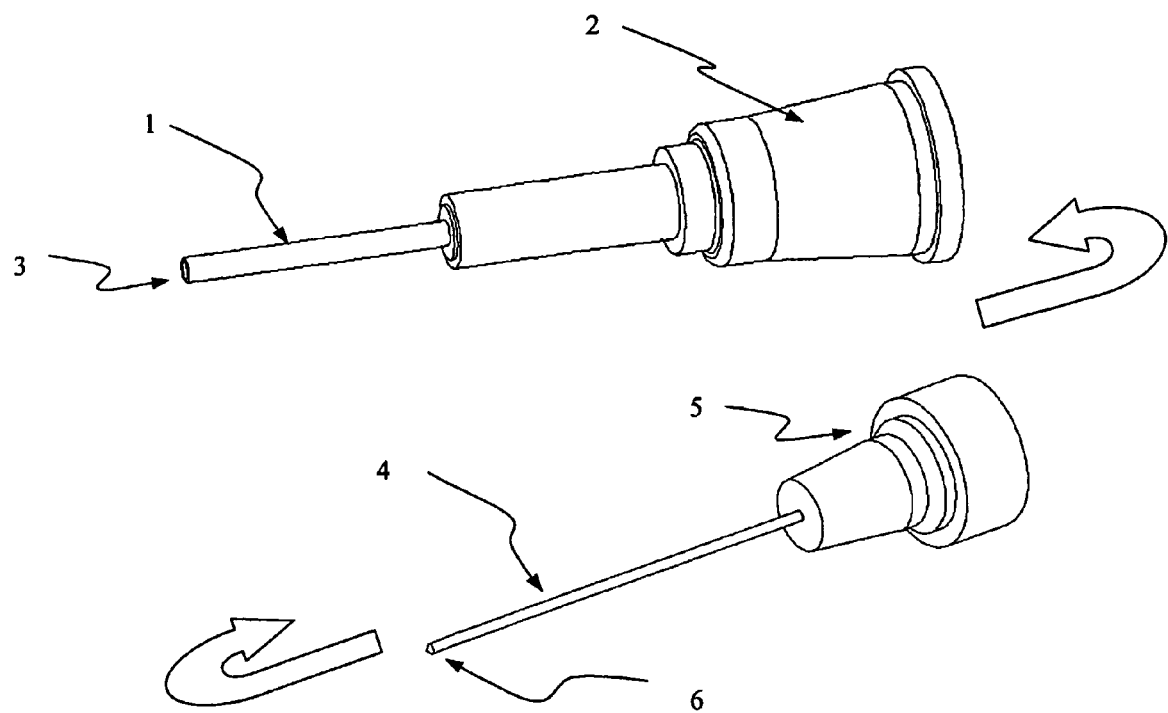
FIG. 1 shows an exploded view of the outer sheath microcannula and the inner member of the ophthalmic microsurgical system.

FIG. 1 shows an exploded view of the ophthalmic microsurgical system of the present invention. The ophthalmic microsurgical system comprises a thin walled outer sheath microcannula 1 with a connector 2 at the proximal end, a distal tip 3 and a communicating channel between. The microcannula outer sheath 1 is disposed about an inner member 4, which fits and slides within the channel of the microcannula 1, the inner member 4 comprising at least a proximal end 5 and a distal tip 6. FIG. 3 shows an assembled view of the ophthalmic microsurgical system with the inner member 4 inserted through the channel of the outer sheath microcannula 1. The inner member 4 is designed to extend beyond the distal tip 3 of the microcannula 1 a specified distance depending upon the requirements of the specific inner member 4. FIG. 4 is an enlarged detail drawing showing the distal tip 6 of the inner member 4 extending a specified distance beyond the distal tip 3 of the microcannula 1. The inner member 4 may comprise a trocar, needle or microsurgical tool and may also be used to transport fluids, energy, sensors, or gases. The tissues of the eye along the tissue tract may be treated in discrete regions by using the outer sheath to localize the site of action for the inner member. Different configurations of inner members 4 may be used in sequence with the outer sheath 1 to accomplish different surgical tasks.

The microcannula 1 may be introduced manually or as part of a system to provide surgical support or guidance. The microcannula 1 may be inserted into an existing tissue tract of the eye such as Schlemm's Canal, aqueous collector channels, and aqueous veins, or may be used to create a tract within tissues of the eye such as the sclera. The positioning of the microcannula 1 in tissues such as Schlemm's Canal can be verified by several means including such means as a change in pressure/vacuum resistance in the surrounding environment as the system enters the Canal, a change in tissue color of the tissues of the Canal, direct visual location during surgical cut-down or by external image guidance. Accurate positioning within the Canal or other eye tissues may be aided by features of the microcannula 1.

Various inner members 4 may be inserted into the microcannula for the progressive steps to introduce the microcannula 1 into a tissue tract such as Schlemm's Canal, advance the microcannula 1 along the tract, and perform surgical intervention of the tissues near the tip 3 of the microcannula 1. Once inserted into a tissue tract, the microcannula 1 may be progressively advanced to the appropriate areas for treatment. The microcannula sheath 1 and inner member 4 for such use are configured to form an assembly with sufficient stiffness to progress along the tissue tract with minimal tissue damage. Tissue damage may induce fibrosis, complicating procedures such as filtration surgery for glaucoma or viscocanalostomy. The microcannula 1, which may be more flexible than the inner member 4, may be advanced into the tissue tract without the inner member 4, to advance the microcannula 1 atraumatically. The distal tip 6 of the inner member is preferred to be limited in extension from the tip 3 of the microcannula 1 to prevent tissue damage. With the increased flexibility and mobility, large sections of Schlemm's Canal or long tissue tracts may be treated from a single access point with the microcannula 1.

Figure 2:
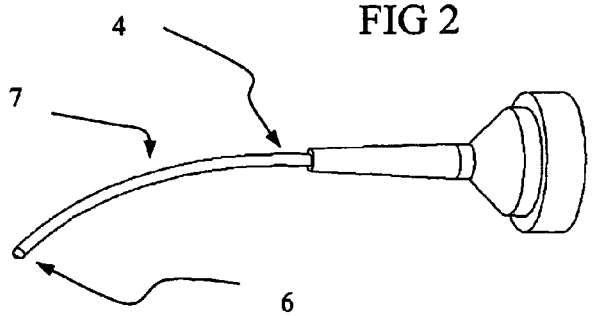
FIG. 2 shows a curved inner member for use with the ophthalmic microsurgical system.

The microcannula 1 may be comprised of a thin walled polymer or metallic tube of sufficient stiffness to allow it to be advanced into tissues or along the tissue tract such as Schlemm's Canal, and sufficient flexibility to follow the radial tract of Schlemm's Canal. The proximal connector 2 may be of a Luer type or similar system for the attachment or introduction of secondary elements, fluids or surgical tools. The proximal connector 2 is preferably configured to allow fluid-tight introduction of materials and tools through the channel of the outer sheath microcannula 1. This can be accomplished with a close sliding fit between the channel of the microcannula 1 and the inner member 4 and/or with a hemostasis seal built into the proximal connector 2. Due to the small size of Schlemm's Canal and other tissue tracts of the eye, approximately 50 to 200 microns in diameter, the microsurgical system must be appropriately sized. Typically, the microcannula 1 is sized in the range of 50-250 microns inner diameter with a wall thickness from 10-100 microns. The length of the microsurgical system can be varied for different applications or for use with different delivery systems and surgical tools. Due to the curvature of a tissue tract such as Schlemm's Canal, the microcannula 1 may be flexible in the appropriate dimensions. In some embodiments, a predetermined curvature 7 may be applied to the inner member 4 and/or the outer sheath 1 during fabrication, as shown in FIG. 2 and in the assembled view of the microsurgical system in FIG. 3. The distal tip 3 of the microcannula 1 is formed so as to provide a smooth entry into the target tissues. Suitable materials for the microcannula 1 include metallic films, polyetheretherketone (PEEK), polyimide, polyamide, polysulfone, nylon, urethane, PTFE, FEP or similar materials. The microcannula 1 may also comprise surface treatments such as lubricious coatings to assist in tissue penetration or reflective coatings to aid in location and guidance during medical imaging.

The microcannula 1 may also have markings on the exterior for assessment of depth in the tissue tract or Schlemm's Canal. The external markings allow user assessment of the length of the tissue tract or Schlemm's Canal accessed by the microcannula 1, and the approximate location of the microcannula tip 3.

Depending on the application, the inner member 4 may be a guide wire, hollow needle, micro-trocar or similar element and comprises a proximal end 5 and a distal tip 6, and may contain a communicating channel between them. The inner member 4 may also comprise sensing means such as a pressure transducer, light pipe or optical fiber to aid in determining location, local fluid pressure, blood flow or other parameters. The inner member 4 is sized correspondingly to fit slidably within the microcannula 1 and therefore will be in the range of 50-240 microns in outer diameter. If hollow, the inner diameter of the inner member 4 will be in the range of 40-210 microns.

In one preferred embodiment for introducing and advancing the microcannula 1 along a tissue tract such as Schlemm's Canal, the inner member 4 may comprise a solid element or wire to provide rigidity with the distal end of the assembly. Highly elastic, high modulus materials such as metals including stainless steel, tungsten and nickel titanium alloys, and structural polymers such as nylon, polyethylene, polypropylene and PEEK are particularly preferred for construction of the inner member 4. The inner member 4 may be shaped to provide curvature to the microcannula 1 or to provide support for lower modulus microcannula materials.

In an alternate embodiment, the distal end 6 of the inner member 4 may be sharpened and adapted to the microcannula 1 to penetrate and guide the microcannula 1 through scleral and other ocular tissues to reach desired locations for surgical intervention such as Schlemm's Canal, or to create tissue tracts for the drainage of aqueous humor. The distal end 6 of the inner member 4 may comprise or alternately hold a sharpened member for such applications. The distal end may be conically tapered 8, as shown in FIG. 5, or beveled or spatula shaped 9, as shown in FIG. 6, to optimize the desired tissue penetration characteristics. The distal tip 6 of the inner member 4 may be designed to penetrate scleral tissues with minimal deflection of the microcannula 1 and surrounding tissues, or it may be shaped in a specific manner to provide a predetermined deflection angle or curvature. For example, a "spatula" or "spade" type faceted cutting tip will provide for straight cutting penetration with minimal tissue deflection, while a conventional suture type triangular cutting tip will provide for deflection in one direction. A hypodermic needle may act as the inner member 4, which provides a sharpened end for penetration while allowing for a working channel to deliver fluids or gases. Preferred materials include stainless steel, tungsten, and nickel titanium alloys.

Once the microcannula 1 is introduced and advanced appropriately into Schlemm's Canal, the inner member 4 may be exchanged for one designed for surgical intervention. The inner member 4 may be disposed such that its distal tip is extensible beyond the distal tip of the microcannula 1. In one embodiment, the inner member 4 comprises a fine wire with a cutting tip to provide support and for the initial introduction of the microcannula 1 into the target tissues. In another embodiment, the inner member 4 comprises a blunt tip 19, as shown in FIG. 3, which is designed to bluntly dissect a tract in the tissue, and is disposed distally from the microcannula 1 for a set distance. Other embodiments involve microsurgical tools and sensors. Each inner member 4 is precisely mated to the inner diameter and proximal coupling of the microcannula outer sheath 1 to provide a high level of surgical control for delicate microsurgery.

Figure 8:
FIG. 8 shows the inner member and surgical tool of FIG. 7 inserted through the outer microcannula of the ophthalmic microsurgical system.
Figure 9:
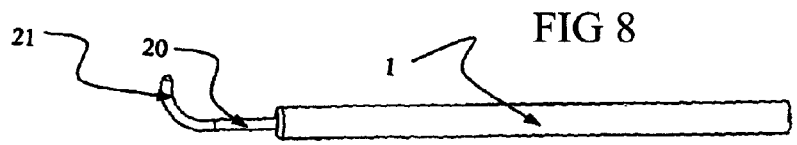
FIG. 9 shows the ophthalmic microsurgical system of FIG. 8 with the surgical tool extended from the inner member.

In another embodiment shown in FIG. 7, the microsurgical system comprises a surgical tool 20 for creating controlled punctures in the trabecular meshwork from within Schlemm's Canal. The surgical tool 20 may be constructed separate from or integral with the inner member 4. The diameter of the surgical tool 20 is such that it may be inserted through the channel of the microcannula 1 or, alternatively, through a channel in a hollow tubular inner member 4. The surgical tool 20 may be comprised of a superelastic material such as a nickel tinanium alloy, and configured such that the distal tip 21 is shaped and bent at an angle with respect to the axis of the inner member 4. The surgical tool 20 is constructed such that the practitioner knows where the angulation of the tip 21 is directed. Features such as markings or guides may be used to provide tip direction. The microcannula 1 is placed into Schlemm's Canal through means as detailed above. When the surgical tool 20 is disposed within the microcannula 1 and/or within a tubular inner member 4, as shown in FIG. 8, the distal tip 21 is straightened. The microcannula 1 is advanced to the location where the surgical puncture is to be created and the surgical tool 20 is advanced within the microcannula 1 until the tip 21 extends from the microcannula 1, bending at the predetermined angle and directed towards the trabecular meshwork, as shown in FIG. 9. The surgical tool 20 is advanced until it penetrates the meshwork and then is withdrawn. The microcannula 1 can then be advanced to the next treatment site. In this manner, size and location of drainage openings can be precisely controlled, providing optimum treatment regimen for the patient. The angle of the tip 21 may be in the range of 45 to 135° from the axis, and the tip 21 may comprise a cutting element as described above.

Figure 10:
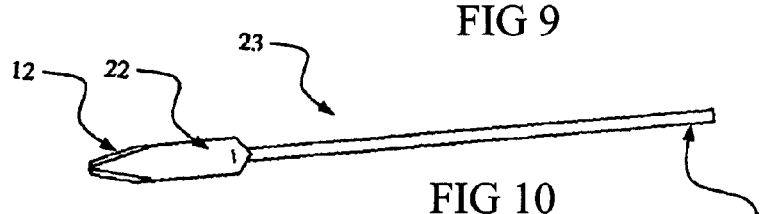
FIG. 10 shows a surgical cutting tool for use with the ophthalmic microsurgical system.

In another embodiment shown in FIG. 10, the microsurgical system includes a surgical cutting tool 23 mountable to or interchangeable with the inner member 4. The surgical cutting tool 23 may utilize a separate penetrating or cutting element such as a diamond or sapphire tip or blade 12. In one such design, a basket 22 is created from wire of a shape memory alloy such as a nickel tinanium alloy. The basket 22 is expanded in order to place a sharpened segment of diamond or sapphire blade 12 or similar element within, and then released to grip the element tightly. The basket 22 may be mounted on the end of a solid element 13 to create a surgical tool compatible with the microcannula 1.

In another embodiment, the inner member 4 may comprise a sensing means. Such means may comprise a stiff tube surrounding a fluid channel for communicating of ambient pressure at the distal tip, or similarly the channel may contain an optical fiber for the transmission and relay of optical signals. Pressures at the distal tip 6 may be used for in situ fluid pressure measurements, or for differential pressure measurements to assist in providing locating means for the microcannula 1. In such a system, the pressure differential will change when the distal tip 6 with the sensing means transits from scleral tissues into the fluid-filled Schlemm's Canal, or into the anterior chamber. Optical sensing may also be used for locating means, or to provide blood flow, blood oxygen, or other sensing parameters. Sensing means may also comprise various tissue or disease sensing means utilizing "chip" type sensors. Suitable materials for an inner member 4 for structural support of a sensing means include but are not limited to stainless steel, nickel tinanium alloy, titanium, and structural polymers such as nylon, polysulfone, polypropylene, polyethylene, and PEEK.

Figure 13:
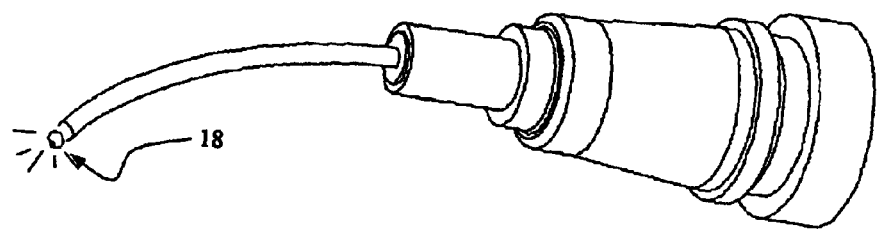
FIG. 13 illustrates an ophthalmic microsurgical system that includes a signaling beacon on the inner member.

Similar to the use of sensing means, the inner member 4 may comprise a signaling beacon 18, as shown in FIG. 13, to identify the location of the microcannula tip 3 relative to the target tissues. The beacon 18 may comprise an echogenic material for ultrasound guidance or a light source for visual guidance. In one embodiment, a beacon 18 comprising a fiberoptic light source emitting 90 degrees from the tip of the microcannula 1 is advanced and rotated along Schlemm's Canal until the light source targets the appropriate tissues such as the trabecular meshwork. The light source may be emitted 45 to 135 degrees from the axis of the microcannula beacon 18 as long as the tissue target area is coincident with the path of the inner member 4.

Figure 11:
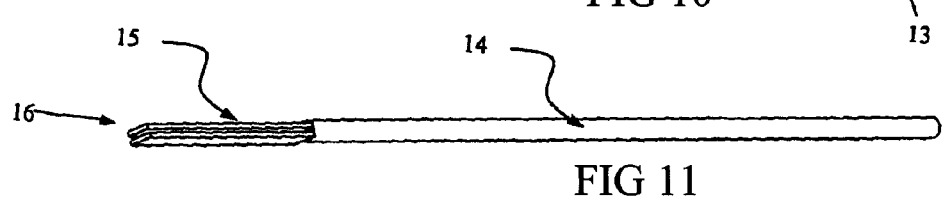
FIGS. 11 and 12 show a dissecting tool for use with the ophthalmic microsurgical system.
Figure 12:
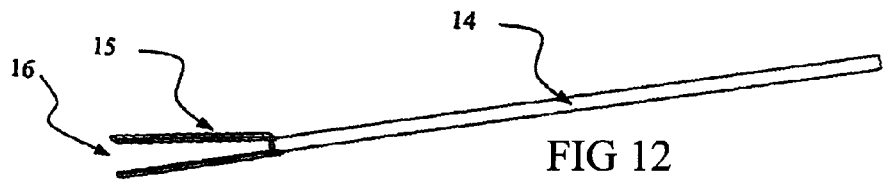

In another embodiment shown in FIGS. 11 and 12, the microsurgical system comprises a surgical tool 16 designed to provide blunt microdissection of tissues for the creation of drainage tracts or the implantation of shunts or similar elements. The surgical tool 16 may be constructed integrally with or interchangeable with the inner member 4. The surgical tool 16 is comprised of a conductive shaft 14 and a distal tip configured with two or more splines 15 constructed of a shape memory alloy. The splines 15 are fabricated such that a bipolar memory shape set is applied to them. In the first configuration shown in FIG. 11, the splines are gathered together on the axis of the shaft 14. In the second configuration shown in FIG. 12, the splines 15 are angled outward from the axis of the shaft 14. The splines 15 are transitioned from one configuration to the other by a square wave electrical voltage applied to the conductive shaft 14 by an electronic controlling system. The pulsing of the voltage induces the phase transformation of the splines 15, causing them to open and close rapidly. As the surgical tool 16 is advanced through the tissue, the opening and closing splines 15 bluntly dissect a microtract.

In another embodiment, the microcannula 1 is used to access or create a tissue tract in the eye and subsequently used to deliver an implant to the tract. The implant may comprise stent-like devices to hold open tissue spaces or drug eluting materials to provide localized drug delivery. An implant such as a tubular stent, may be loaded into the lumen of the microcannula 1 in a compressed or folded state and the inner member used to deploy the implant at the desired location. In another embodiment, a stent-like implant may be previously attached to the microcannula body or comprise the distal portion of the microcannula, and deployed by mechanical action of the inner member. An inner member or surgical tool may be used to create or access a tissue tract with the microcannula implant mounted on it.

EXAMPLES

Example 1

A microcannula system was fabricated for experimentation on ex-vivo human eyes obtained from an eye bank. The microcannula consisted of a 30 gauge tubing adapter (Small Parts, Inc., Miami Lakes, Fla.) with a distal tip comprised of polyimide tubing bonded into the lumen of the tube adapter. The tube adapter is a standard hypodermic needle, cut to ½" (12.5 mm) length with a perpendicular (straight) cut distal end and a female Luer at the proximal end. The tube adapter has an inner diameter of 150 microns and an outer diameter of 300 microns. A section of polyimide tubing (MicroLumen, Tampa, Fla.) with inner diameter of 110 microns and a wall thickness of 14 microns was bonded into the distal tip of the tube adapter with cyanoacrylate adhesive and allowed to cure overnight. Assemblies were fabricated with 1.0 and 1.5 cm of polyimide tubing extending from the tube adapter. A 2 cm section of stainless steel wire (Fort Wayne Metals, Fort Wayne, Ind.) 100 microns diameter was mounted onto a Luer cap for attachment to the Luer connector of the microcannula. The wire tips were hand ground to a spade type point and a tapered cone type point. In some assemblies, the stainless wires were bent by hand into a curve of approximately 14 mm radius, to allow easier advancement through the curvature of Schlemm's Canal.

Ex-vivo human eyes were used to perform experiments with the cannulae. The human eyes were placed under a stereomicroscope. Using ophthalmic scalpels, successive layers of the sclera were cut away until Schlemm's Canal was located. Various examples of the microcannula system were successfully guided into the Canal. When the tip of the microcannula was into the ostium of the Canal approximately 1-2 mm, the inner member was removed. The microcannulae were advanced to determine their ability to track the Canal. In all cases the microcannulae were able to be advanced at least 1 cm or more into the Canal. If the wire is left in place, the curved wires allowed for advancement into the Canal while the straight wires were only able to be advanced a short distance.

In a second experiment, the microcannulae were evaluated for the ability to pierce the scleral tissues. The system with a distal tip in a tapered cone had difficulty in penetrating the tissues, causing tissue deformation and requiring a fair amount of force to begin penetration. The tip ground in a spade type distal end was able to penetrate the tissues with much less deformation.

In a third set of experiments, ophthalmic suture needles with different tip configurations were used to pierce the sclera to assess the differences in terms of tissue and needle deflection. The suture needles (Surgical Specialties, Reading, Pa.) used were Center Point Spatula and Side Cutting Lancet. In each trial the spatula point allowed easiest penetration with minimal tissue deflection.

Example 2

In another example, a surgical tool to provide for controlled punctures in the trabecular meshwork was created using Nitinol (nickel titanium alloy) wire, 0.004" (100 microns) diameter (Ft. Wayne Metals, Ft. Wayne, Ind.). The wire was formed with a 10 mm diameter curve for the distal 3 cm. The distal 2 mm of the tip was further formed with a small radius bend at approximately 90 degrees from the axis of the wire, directed toward the inside and remaining in the plane of the curve.

A microcannula was fabricated comprised of a 3 cm long polyimide tube (Microlumen, Tampa, Fla.), with an inner diameter of 140 microns and an outer diameter of 200 microns, adhesively bonded to a section of 26 gauge hypodermic tubing (Small Parts, Inc, Miami Lakes, Fla.). The hypodermic tubing was mounted in a short plastic sleeve for ease of manipulation. The polyimide tubing was heat set with a curvature of approximately 2.5 cm. A stainless steel guiding sheath was fabricated from sections of hypodermic tubing (Small Parts, Inc, Miami Lakes, Fla.) to create a stepped sheath with an inner diameter of approximately 300 microns. The guiding sheath was cut to 10 mm long and the mounted in a plastic shaft. The guiding sheath was mounted at the distal end of the shaft and at a right angle to the shaft axis. This configuration of the sheath allowed for the tip of the guiding sheath to be directed at Schlemm's Canal by one hand, while the cannulation was performed by the other hand, which provided better positioning control for the procedure.

An ex-vivo human eye was placed in a holding cup and positioned under a stereomicroscope. A rectangular flap was cut approximately 4 mm on a side at the limbus. The flap was excised to approximately ½ scleral thickness. The tissue bed was further dissected to reveal Schlemm's Canal, and the Canal was de-roofed to allow access. The microsurgical tool was loaded into the microcannula by advancing the tool proximal end into the cannula distal end and continuing until the proximal end could be grasped at the proximal end of the cannula. The tool was oriented so that the curvature of the bend was approximate to the curvature of Schlemm's Canal. The tool was then withdrawn into the cannula approximately 3 mm, and the tip of the microcannula was inserted into the proximal end of the guiding sheath. Under the microscope, the distal tip of the guiding sheath was placed at the ostium of Schlemm's Canal. The microcannula was advanced into the canal approximately 30 degrees. While holding the microcannula steady, the tool was advanced slowly until the distal tip extended beyond the cannula tip and pierced the trabecular meshwork. The distal tip of the tool could be observed through the cornea, entering the anterior chamber. The microcannula was withdrawn slightly, further tearing the trabecular meshwork. The tool was then withdrawn into the cannula and the system withdrawn from the Canal.

Example 3

In another example, a signaling means for determining the location of the microcannula distal tip was fabricated. A small battery powered laser diode light source illuminator was constructed, with the diode operating in the visible red light range. A single plastic optical fiber (POF) (South Coast Fiber Optics, Achua, Fla.) of approximately 100 microns in diameter and 20 cm in length was mounted to an adapter which provides adjustable alignment capabilities to bring the fiber tip into the focus of the laser illuminator. The POF distal tip was cut flat, and hence the illumination was directed toward all radial angles from the tip. A cylindrical handpiece mount was fabricated to hold a microcannula. The microcannula was constructed of nylon with dimensions of approximately 120 microns inner diameter and 180 microns outer diameter. The operative end of the microcannula was 15 mm in length and the proximal end was flared for mounting on the handpiece. The fiber is disposed through the handpiece and within the microcannula as detailed in Example 1, and the fiber adapter mounted to the laser illuminator. The adapter alignment was adjusted to provide the brightest spot at the end of the POF.

Ex-vivo human eyes were surgically dissected with a small rectangular flap at the limbus to reveal Schlemm's Canal. The microcannula and light fiber were advanced into the canal with the light source on. The illuminated tip of the fiber was seen through the scleral tissues and also from the anterior chamber of the eye through the trabecular meshwork. In multiple trials, the microcannula with beacon tip was able to be advanced up to 120° around from the access point within Schlemm's Canal.

Example 4

In another example, a microcannula is used to access Schlemm's Canal as described in example 1. The tip of the microcannula is positioned at the desired location along Schlemm's Canal for treatment. The inner member is removed while keeping the outer microcannula sheath in position. A stent type of implant is folded or compressed and inserted into the lumen of the microcannula. The stent is releasably secured to the distal end of an inner member, and pushed along the microcannula lumen by the mechanical action of the inner member. When deployed out from the end of the microcannula into the tissue tract, the stent is expanded and is released from the inner member. The microcannula is moved to another location along Schlemm's Canal for delivery of another implant as desired.

What is claimed is:

1. A microcannula based microsurgical system designed to operate within a tissue tract of the eye, comprising:
   a flexible tubular outer sheath with an outer diameter of 250 microns or less, with proximal and distal ends, to fit within the tissue tract;
   a proximal connector on the outer sheath for introduction of materials and tools;
   and an inner member with a proximal end and a distal tip, wherein the tip is restricted from advancement past a predetermined length from the outer sheath, with the outer sheath and inner member sized such that the inner member fits slidably within the outer sheath and may be removed separately from the outer sheath while in the tissue tract.

2. A microsurgical system of claim 1, wherein the tissue tract is Schlemm's Canal of the eye.

3. A microsurgical system of claim 1, wherein the tissue tract is created by the flexible outer sheath and inner member.

4. The microsurgical system of claim 1, wherein the microsurgical system provides blunt dissection of the tissue tract.

5. The microsurgical system of claim 1, wherein the flexible tubular outer sheath comprises polyimide or a fluoropolymer.

6. The surgical system of claim 1, wherein the flexible tubular outer sheath is curved in the range of 10-15 mm diameter.

7. The microsurgical system of claim 1, wherein the inner member comprises nickel titanium alloy.

8. The microsurgical system of claim 1, wherein the inner member comprises tungsten.

9. The microsurgical system of claim 1, wherein the inner member is curved in the range of 10-15 mm diameter.

10. The microsurgical system of claim 1, further comprising a tool to cut or ablate tissues that interchanges with the inner member to position the tool tip to a predetermined position from the tip of the flexible tubular outer sheath.

11. The microsurgical system of claim 1, wherein the inner member has a distal tip that is shaped for tissue dissection.

12. The microsurgical system of claim 11, wherein the distal tip comprises a multi-faceted shape or a tapered conical shape.

13. The microsurgical system of claim 11, wherein the distal tip is sharpened for tissue penetration.

14. The microsurgical system of claim 11, wherein the distal tip is shaped to provide for controlled surgical penetration of the trabecular meshwork.

15. The microsurgical system of claim 14, wherein the distal tip advances and penetrates the trabecular meshwork from a 45 to 135 degree direction from an axis of the outer sheath.

16. The microsurgical system of claim 1, wherein the outer sheath additionally comprises a plurality of markers set at regular intervals such that each marker is spaced from adjacent markers by a fixed distance along the outer sheath to provide depth measurement.

17. The microsurgical system of claim 1, wherein the inner member comprises a sensing means.

18. The microsurgical system of claim 1, wherein the inner member comprises a signaling means.

19. The microsurgical system of claim 18, wherein the signaling means is an optical fiber.

20. The microsurgical system of claim 19, wherein the optical fiber directs illumination away from an axis of the microcannula at an angle of 45 to 135 degrees.

21. The microsurgical system of claim 20, wherein the optical fiber directs illumination to coincide with the target of an inner member directed away from the axis of the microcannula at an angle of 45 to 135 degrees.

22. The microsurgical system of claim 19, wherein the optical fiber directs illumination away from the axis of the microcannula at an angle of approximately 90 degrees.

23. The microsurgical system of claim 1, wherein the system is sized to deliver an implant to the tissue tract by action of the inner member.

24. The microsurgical system of claim 23, wherein the implant is a stent-like tube.

* * * * *